United States Patent [19]  [11] Patent Number: 4,977,896
Robinson et al.  [45] Date of Patent: Dec. 18, 1990

[54] ANALYSIS OF BIOLOGICAL SIGNALS USING DATA FROM ARRAYS OF SENSORS

[75] Inventors: Stephen E. Robinson, San Diego; William C. Black, Jr., Del Mar, both of Calif.

[73] Assignee: Biomagnetic Technologies, Inc., San Diego, Calif.

[21] Appl. No.: 359,640

[22] Filed: May 26, 1989

[51] Int. Cl.$^5$ .............................................. A61B 5/05
[52] U.S. Cl. .............................. 128/653 R; 128/731; 324/245; 324/248
[58] Field of Search ................ 128/653, 731; 324/245, 324/248

[56] References Cited

U.S. PATENT DOCUMENTS

| | | | |
|---|---|---|---|
| 4,309,659 | 1/1982 | Yoshii | 324/345 |
| 4,731,582 | 3/1988 | Posseme et al. | 324/245 |
| 4,736,751 | 4/1988 | Gevins et al. | 128/731 |
| 4,793,355 | 12/1988 | Crum et al. | 128/653 R |

Primary Examiner—Lee S. Cohen
Assistant Examiner—Krista M. Pfaffle
Attorney, Agent, or Firm—Gregory O. Garmong

[57] ABSTRACT

Signals produced by brain activity are measured by each sensor of an array of magnetic and/or electrical sensors external to but proximate to the head (or other portion of the body) of a subject. The measurements obtained simultaneously from all of the sensors are combined in a manner to permit selective measurement of the electrical activity from a specified location within the body, or alternatively, to permit the location in the body producing a particular type of response to be identified. The instantaneous measurement of each sensor is scaled by a weighting coefficient for that sensor, and the products added over all of the sensors. The weighting coefficients are calculated from a mathematical model of the brain that includes information on the shape of the potential source, the extent or type of source activity, the electrical and magnetic properties of the media, and the locations and orientations of the sources and the sensors.

14 Claims, 6 Drawing Sheets

ANALYSIS OF BIOLOGICAL SIGNALS USING DATA FROM ARRAYS OF SENSORS

BACKGROUND OF THE INVENTION

This invention relates to the measurement of electromagnetic signals originating in the human body, and, more particularly, to the measurement of magnetic and/or electrical fields originating from brain activity.

The human body produces various kinds of energy that may be used to monitor the status and health of the body. Perhaps the best known of these types of energy is heat. Most healthy persons have a body temperature of about 98.6° F. A measured body temperature that is significantly higher usually indicates the presence of an infection or other deviation from normal good health. A simple medical instrument, the clinical thermometer, has long been available to measure body temperature.

Over 100 years ago, medical researchers learned that the body also produces electrical signals. Doctors today can recognize certain patterns of electrical signals that are indicative of good health, and other patterns that indicate disease or abnormality. The best known types of electrical signals are those from the heart and from the brain, and instruments have been developed that measure such signals. The electrocardiograph measures electrical signals associated with the heart, and the electroencephalograph measures the electrical signals associated with the brain. Such instruments have now become relatively common, and most hospitals have facilities wherein the electrical signals from the bodies of patients can be measured to determine certain types of possible disease or abnormality.

More recently medical researchers have discovered that the body produces magnetic fields of a type completely different than the other types of energy emitted from the body. The research on correlating magnetic fields with various states of health, disease and abnormality is underway, but sufficient information is available to demonstrate that certain emitted magnetic fields are associated with conditions such as epilepsy Present medical studies are investigating the nature of the normal and abnormal magnetic fields of the brain, and seeking to correlate those fields with brain functions and patient health.

For example, if it were known that a particular condition, such as epilepsy, were associated with an abnormal magnetic field produced at a particular location in the brain, then it might be possible to detect the abnormality at an early stage, before the condition became acute, and then apply other medical knowledge to treat or surgically remove that precise portion of the brain with minimal side effects on the patient. A selective measurement of brain activity could also permit more precise use of drugs to control the condition. Magnetic studies of the brain therefore offer the potential for understanding and treating some of the most crippling diseases and conditions known.

The biomagnetometer is an instrument that has been developed for measuring magnetic fields produced by the body, particularly the brain and heart. The biomagnetometer is a larger, more complex instrument than the medical instruments mentioned earlier, primarily because the magnetic fields produced by the body are very small and difficult to measure Typically, at 1 centimeter from the head, the strength of the magnetic field produced by the brain is about 0.000000001 Gauss. By comparison the strength of the Earth's magnetic field is about 0.5 Gauss, or five hundred million times larger than the strength of the magnetic field of the brain. Most electrical equipment also produces magnetic fields, in many cases much larger than that of the Earth's field. It is apparent that, unless special precautions are taken, it is not possible to make magnetic measurements of the human body because the external influences such as the Earth's magnetism and nearby apparatus can completely overwhelm and mask the magnetic fields from the body.

The biomagnetometer includes a very sensitive sensor for magnetic signals. The currently most widely used sensor is a superconducting Quantum Interference Device or SQUID, which is sufficiently sensitive to detect magnetic signals produced by the brain. (See, for example, U.S. Pat. Nos. 4,386,361 and 4,408,189, whose disclosures are incorporated by reference, for descriptions of two types of SQUIDS.) This detector and its associated equipment require special operating conditions such as a cryogenic dewar, and cannot be placed into the body or attached directly to the surface of the body.

The present biomagnetometer therefore provides a chair or table for the patient, and a structure which places the detector in proximity with the head of the patient, as about 1-2 centimeters away. Special electronics is provided to filter out external effects such as the Earth's magnetic field and the magnetic fields of nearby electrical instruments. (For a description of such a device, see U.S. Pat. Nos. 3,980,076 and 4,079,7S0, whose disclosures are herein incorporated by reference.) The patient and detector can also be placed into a magnetically quiet enclosure that shields the patient and the detector from the external magnetic fields. (For a description of such an enclosure, see U.S. Pat. No. 3,557,777, whose disclosure is herein incorporated by reference.) With these special precautions, medical researchers and doctors can now make accurate, reliable measurements of the magnetic fields produced by the brain, and are studying the relationship of these fields with diseases and abnormalities.

It is well established that certain physically identifiable locations in the brain are responsible for specific types of activities and functions. It is therefore important to correlate the measured biomagnetic field with the particular location in the brain which produces the field. Such a correlation is important to understanding the mechanism by which disease and disorder arise, and also to the treatment of the problem.

Correlating the spontaneous measurement taken by an external array of magnetic or electrical sensors with brain activity at a specific location within the brain is difficult, primarily because other areas of the brain continue to function and produce their own magnetic and electrical fields, even as a measurement is being taken with the intent of measuring activity at a specified location, and because the measurement sensors and instrumentation produce noise that may be of the same magnitude as the signals to be measured It is not easily determined whether a particular signal measured externally originates at the selected location, other locations, or jointly at the selected location and other locations, or in fact is a manifestation of instrument noise. At the present time, there is a good deal of reliance on averaging multiple occurrences of magnetic and/or electric signals synchronously with external events such as a stimulus, to isolate the origin of particular magnetic signals.

Moreover, it is difficult to develop data from spontaneous brain activity, having a high signal to noise ratio, that can reliably be said to originate at a selected location in the brain. Having such a capability would be extremely useful, because it would permit studies of neurological disorders associated with epilepsy, stroke, and head injury, for example, and even direct physiological studies of some of the most basic phenomena of life, such as attention and boredom, mental disorders, language comprehension and expression, and response to external stimuli.

An important step in correlating external measurements with the specific locations of internal events is disclosed in U.S. Pat. No. 4,793,355, whose disclosure is incorporated by reference, and which provides a methodology for automatically tracking the position of the sensors in respect to the position of the head of the patient. When used in conjunction with the known spatial sensitivity profile of the detector and either an external stimulus or synchronization with voluntary activity, this approach gives important information about the internal origin of the externally measured signal. This technology, by itself, is limited in its resolution of location and nature of the source, because of various types of noise and the continued operation of other brain functions as measurements are taken. It is also limited in its ability to investigate spontaneous, non-evoked brain activity.

There is therefore a need for an improved approach for measuring biomagnetic fields and correlating those fields with their source location within the brain. Preferably, such an approach would permit data to be simultaneously obtained for a number of different signals produced from sensors in a number of different locations, to permit correlation of all signal information. The approach also must achieve a high signal to noise ratio that permits the signal of interest to be discerned and isolated relative to other brain signals, external noise, and instrument noise. The present invention fulfills this need, and further provides related advantages.

SUMMARY OF THE INVENTION

The present invention provides an approach for analyzing electromagnetic signals, such as magnetic and electrical fields, produced by the body. It permits selection of the location within the body from which the signals are to be examined, and an excellent characterization of the signals themselves with an optimized signal to noise ratio. The approach can be practiced with existing hardware, or can utilize apparatus that is specially designed for the purpose.

The present invention further provides an approach for utilizing multiple electromagnetic sensors of an array in combination to obtain better information about the functioning of an electromagnetic source within the body, than could be obtained from the uncombined data of the individual sensors of the array. It provides an approach for mathematically combining the outputs of the sensors of the array in a manner that effectively defines a virtual sensor which is optimized for measuring a particular location within the body, based upon the characteristics of the sensors, the sources, and the body, and their relative locations. The outputs of the individual sensors are weighted and added together to define the virtual sensor output, and different virtual sensors can be defined from a fixed sensor array by modifying the weighting factors according to a mathematical model.

In accordance with the invention, a process for sensing and evaluating signals emanating from the brain of a subject comprises the steps of providing an array of field sensors disposed external to the head of a subject at known locations; measuring the signal strength detected by each sensor of the array; multiplying the signal strength measured by each sensor times a weighting coefficient for that sensor to determine a virtual sensor contribution for each sensor of the array; and adding together the virtual sensor contribution of each of the sensors, to define a virtual sensor signal.

Alternatively stated, a process for sensing and evaluating signals emanating from the body of a subject comprises the steps of measuring a signal strength detected by each sensor of an array of electromagnetic sensors placed proximately to the body of a person; and calculating a virtual sensor signal for the array, as the sum, over the sensors, of the product of a weighting coefficient for each sensor times the signal measured for that sensor.

In yet another form, a process for sensing and evaluating electromagnetic signals emanating from the body of a subject comprises the steps of providing an array of electromagnetic field sensors disposed external to the body of a subject at known locations and orientations; determining a weighting coefficient applicable to each sensor of the array, the step of determining including the steps of characterizing the geometry of the body, characterizing the nature of the electromagnetic fields emanating from possible sources in the body, characterizing the medium through which the electromagnetic fields propagate, formulating a mathematical model of the response of the array of electromagnetic sensors to a source within the body, and calculating the weighting coefficients from the model; measuring the signal strength detected by each sensor of the array; multiplying the signal strength measured by each sensor times the calculated weighting coefficient for that sensor to determine a virtual sensor contribution for each sensor of the array; and adding together the virtual sensor contribution of each of the sensors, to define a virtual sensor signal.

The present invention utilizes the combined response data gathered by each one of an array of sensors external to the body. The sensors can be sensitive to magnetic fields or electrical fields, and the term "electromagnetic" is used herein as a generic descriptor for signals, detectors, or the like to encompass both types of phenomena. The combined data can be treated to attain an optimized characterization of the signal produced from a selected location in the brain or other source. By combining the same response data of the sensors in different ways, simultaneous occurrences in different parts of the body can be understood by themselves and in relation to each other. The present approach can be used to measure any portion of the body from which electromagnetic signals originate, including but not limited to the brain, the heart, muscle tissue, nerves, etc.

To calculate the virtual sensor signal corresponding to an electromagnetic field generated at a selected location in the brain, the signal strength measured by each sensor at a point in time is multiplied by a weighting coefficient determined for that sensor, and then all the products of signal strength and weighting coefficient are added together. The weighting coefficient is calculated from a mathematical model of the body for production of electromagnetic fields. The model typically includes information as to the physical structure and geometry of the portion of the body producing the signal, the nature of the field source operating at the selected location, the relative positions and orientation of the sensors and the selected location in the body, and the spatial sensitivity of the sensor, known as its lead field. From this last component comes the term used to describe this type of analysis, "lead field synthesis" ("LFS").

One desirable feature of this approach is that the nature of the virtual sensor, attained from the weighted combination of the signals of the individual physical sensors, can be changed to tune the response of the virtual sensor to different locations, using the same measured data. Thus, with a first set of weighting coefficients, the virtual sensor is directed to sample a first location in the body, and with a second set of weighting coefficients, the virtual sensor is directed to sample a second location in the body, in both cases using one set of actual measurement data from the physical array of sensors.

Another desirable feature is that the virtual sensor may be tuned for an optimal signal to noise ratio for a particular location, again through the mathematical model that provides the weighting coefficients. The signal to noise ratio is improved by making the virtual sensor less sensitive to brain activity in regions that are not of interest, or by reducing the effective instrument noise. This capability permits the virtual sensor to utilize sophisticated signal acquisition and processing theories already known but never applied to the understanding of the body. The virtual sensor provides a means of combining data from both magnetic and electrical field sensors into a virtual sensor whose measurement units are source strength. This combination renders the measurement of activity independent of the type of sensor or the sensor location.

The virtual sensor signal can be interpreted as the amount of the signal strength measured by all sensors simultaneously which could have originated at a specified source within the brain, to which the virtual sensor is directed.

The approach of the invention may be used with existing biomagnetometers such as that disclosed in U.S. Pat. No. 4,793,355 and available commercially from Biomagnetic Technologies, Inc., San Diego, CA. These biomagnetometers provide up to 14 SQUID-type sensors in an array placed at various positions around the head of the subject under study. The response signal of each sensor is recorded separately, and combined using the approach just described to calculate a virtual sensor response. However, it is possible that other arrays of sensors may be devised that are optimally placed for utilization of the lead field synthesis methodology. In particular, it is expected that larger arrays of electromagnetic sensors, measuring magnetic and electrical signals, will provide even more precise information about the magnitude of signals originating at a particular location within the body.

Other features and advantages of the present invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENT

The approach of the present invention can be used in conjunction with measurements of magnetic and electrical signals from any and all parts of the body. Signals produced from the brain are of great interest, and the preferred embodiment is directed toward this application. The methodology, however, is more generally applicable, as long as an appropriate mathematical model is selected and implemented for each particular application.

Figure 1:
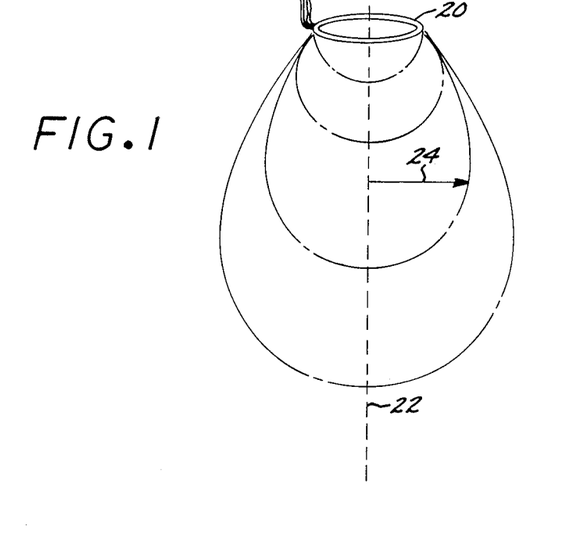
FIG. 1 is a schematic representation of the sensitivity of a single-loop magnetic sensor.

Sensors used to detect magnetic or electrical signals generated in the brain, like all such sensors, are directional in nature and have a sensitivity to signals that depends on the physical position of the sensor relative to the location whereat the signal originates, the orientation of the sensor, and the nature of the source of the signal. Generally, as illustrated in FIG. 1 for a single loop magnetic field sensor 20, the further the origin of the signal from the sensor, the less sensitive the sensor is to the signal. Sensitivity, as represented by the curves of the figure extending below the sensor 20, decreases with increasing axial distance along the axis 22 of the loop, and also with radial distance 24 from the axis 22. The pattern of Figure is illustrative of such sensitivity variations.

Another aspect of the design of sensors is that the larger the loop of the sensor, the more sensitive it should be to measuring small uniform magnetic fields, because more magnetic flux lines can pass through the loop. However, the placement of the sensor also influences its sensitivity to particular signals.

If one knows beforehand the location of the origin and the orientation of a specific signal to be measured, an optimal design and placement for the sensor used to measure the signal can be selected. However, such is not possible for a general-purpose approach, nor is it possible where signals from many locations are to be measured simultaneously or nearly simultaneously.

Figure 2:
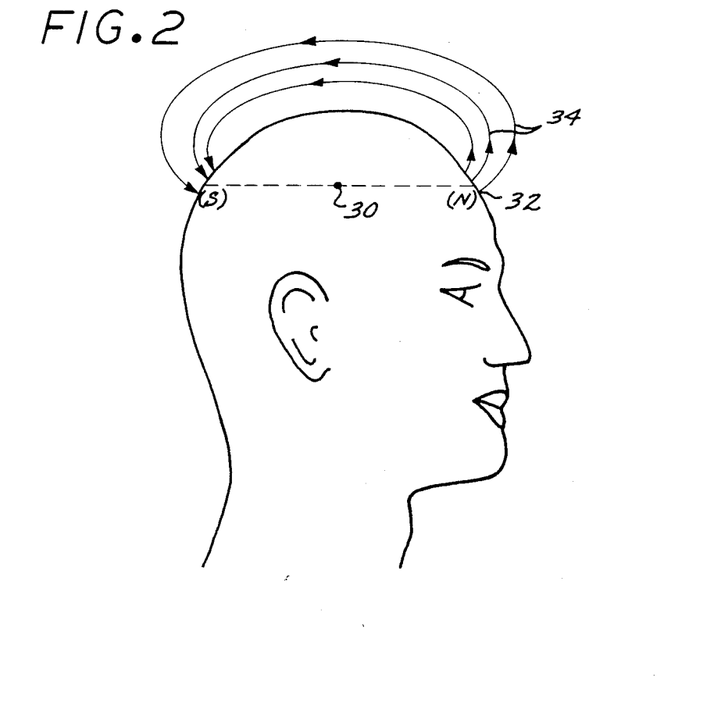
FIG. 2 is a schematic diagram of the magnetic field of a source in the brain.

The following example illustrates the principles of sensor selection for a known source in the brain. The brain generates magnetic signals as a result of electrical currents that originate within the brain. FIG. 2 illustrates the magnetic field produced by a source 30 within the head 32 of the person. The field originating at source 30 is produced by a neural current passing in the direction perpendicular to the page, along a group of neurons located at source 30. Magnetic field lines 34 emerge from the skull to the external environment, where a sensor may be located.

Figure 3:
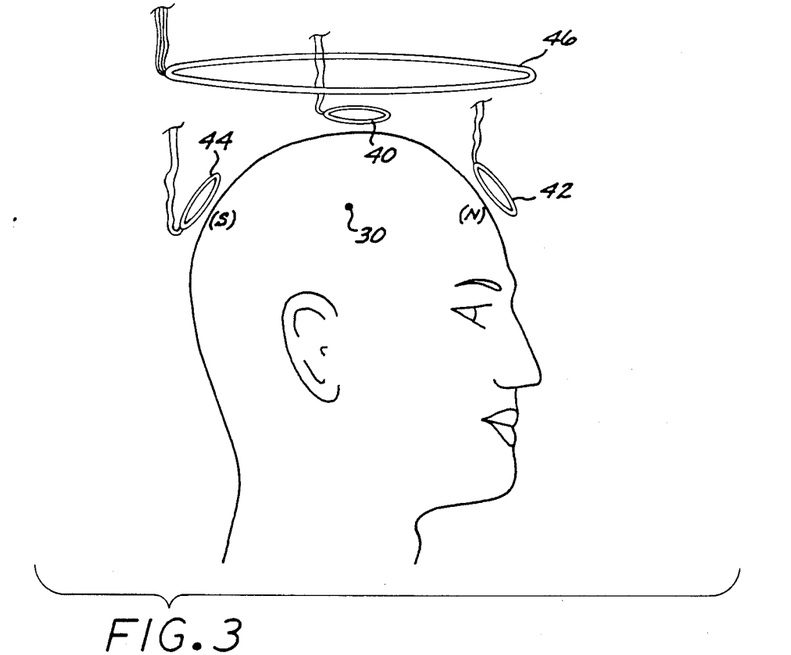
FIG. 3 is a schematic diagram of the placement of sensors to measure the magnetic field of a source in the brain.

FIG. 3 shows the same source 30, but with some external loop sensors positioned to measure the magnetic field. A sensor 40, positioned directly over the current source 30, registers no signal because no magnetic field lines 34 (omitted from FIG. 3, but the same as in FIG. 2) pass through the loop of the sensor 40. A sensor 42 is located above the N pole, and registers a maximum positive signal. A sensor 44 is located above the S pole, and registers a maximum negative signal. A much larger sensor 46, symmetrically located with respect to the N pole and the S pole, although more sensitive to uniform magnetic fields, registers no signal because the net flux through the loop of the sensor is zero.

Figure 4:
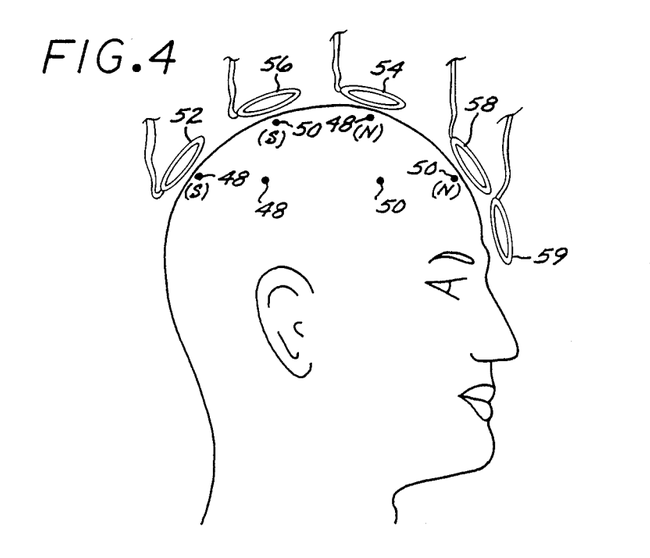
FIG. 4 is a schematic diagram of the placement of sensors to measure the magnetic field of different sources in the brain.

The actual problem faced in making measurements of signals originating in the brain is that, unlike the example illustrated in FIGS. 2 and 3, the location and orientation of the signal source is not known. FIG. 4 illustrates the nature of the sensing problem where there are two sources, and also the origin of the present analytical approach. Where there are two sources 48 and 50, sensors 52 and 54 placed over the 48N and 48S poles for source 48 will be most sensitive to that source, but will also detect some signal due to the other source 50. Likewise, sensors 56 and 58 placed over the 50N and B0S poles for source 50 will be most sensitive to the source 50, but will also detect some signal due to the other source 48. A sensor B9 may be placed so that it does not provide much information about either of the sources 48 and 50.

Thus, if there were a way to utilize the readings of sensors 56, 58, and 59 so as to render the measurements of sensors 52 and 54 insensitive to source 50, an optimal measurement of source 48 could be obtained. This result can be accomplished by subtracting the interfering signal arising from source 50, as best detected by sensors 56 and 58, from the signals detected by sensors 52 and 54, which respond maximally to the desired source 48. Thus, by knowing the proportions and sign with which to combine the signals from all sensors, an optimal measurement can be obtained for a specified source, and interference from unwanted sources can be suppressed. A similar principle holds for obtaining an optimal measurement from source 50 by utilizing the sensors 56 and 58, which convey information primarily about source 50, and sensors 52, 54, and 59, which convey information primarily from the source 48.

Even for the relatively simple example of FIG. 4, the problem of sensing becomes more difficult if none of the sensors are located at the optimal positions for measuring the field of a selected source location and orientation. If none of the sensors of the array 52, 54, 56, 58, and 59 are optimally placed to measure a selected source, then some method must be chosen to utilize the data from some or all of the sensors in order to measure that source.

In principle, the sensitivity of the array of sensor 54, 56, 52,58, and 59 can be adjusted or "tuned" to be optimally sensitive to signals originating from sources in the brain of particular locations and orientations. The approach for achieving such tuning is apparent from the very simple example of FIG. 4, where the locations and orientations of the sources 48 and 50 were specified. The approach is not apparent for the more complex case of millions of sources of signals in the brain having locations and orientations that are not known beforehand, where a relatively small number of sensors are present in the array of sensors, and where there is no prior knowledge that the sensors are optimally placed for measuring a signal.

The present invention provides a technique for utilizing the data produced by an array of sensors to synthesize a "virtual" sensor that is optimally sensitive to a selected source within the body.

Considering both the spatial sensitivity of the sensor, as illustrated in FIG. 1, and the geometric realities of sensor placement, as illustrated in FIGS. 2–4, it is apparent that the needs of a general measurement approach result in some apparently contradictory hardware requirements. Small diameter sensors are desirable to achieve good resolution of signals from shallow locations close to the skull, while large diameter sensors are desirable to achieve measurement of deep sources. Sensors should somehow be effectively capable of being repositioned to measure some sources, while remaining stationary to measure those sources for which they are optimally positioned.

Figure 5:
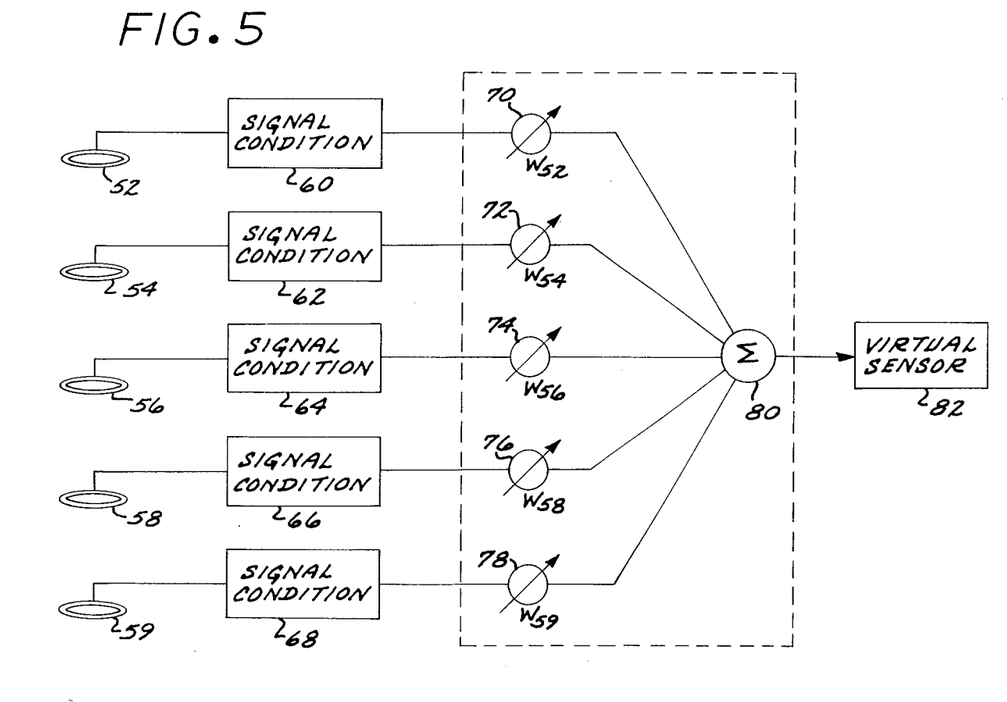
FIG. 5 is a schematic diagram of the manner of combining the measurements of an array of sensor.

The present approach permits these apparently contradictory requirements to be met by utilizing all of the data from the multiple sensors to arrive at a single scalar number that is representative of the magnetic signal produced from a selected location, without physically moving or replacing any of the sensors. As illustrated in FIG. 5, each response signal strength measured by a sensor such as sensors 52, 54, 56, 58, and 59 is first detected and conditioned by filtering and amplifying as necessary, in a signal conditioner depicted as element 60, 62, 64, 66, and 68, respectively. Such detection and signal conditioning apparatus is well known in the art, and is used for existing sensors.

The conditioned signal for each sensor is then multiplied by its own particular signed weighting coefficient, here illustrated as the weighting coefficients $w_{52}$, $w_{54}$, $w_{56}$, $w_{58}$, and $w_{59}$, respectively, in individual multiplying operations 70, 72, 71, 76, and 78. The sign (plus or minus) of the weighting coefficient is taken into account in performing the multiplying operation. A negative weighting coefficient results in a scaled product of polarity opposite to that of the original signal. Each of the resulting arithmetic products is supplied to an adder 80, which adds them together for the five sensors 52, 54, 56, 58, and 59. The resulting sum is supplied as a scalar signal termed a virtual sensor 82. In the preferred approach, the signals from the signal conditioners 60, 62, 64, 66, and 68 are digitized and supplied to a digital computer, which performs the multiplier functions 70, 72, 74, 76, and 78, and the adding function 80, in digital format. (The preceding example dealt with only five sensors, but the present invention is not so limited. Preferably, much larger arrays of sensors are used to improve resolution of sources.)

The effect of the summing of weighted signals approach may be understood with reference to FIG. 4. With regard to the measurement of the magnetic field emanating from the source 48, the sensor 59 would gather almost no useful information, and in fact measure mostly brain noise relative to the source 48. The weighting coefficients of sensor 59 would be a small value The sensors 52 and 54, on the other hand, gather a great deal of information about the source 48, and their weighting coefficients would be large and of opposite sign. The sensors 56 and 58 present the most difficult aspect of the analysis, since they provide some useful information about the source 48, but also a good deal of brain noise resulting from other sources, such as the source 50 (which must be considered noise when one attempts to study the signal produced by the source 48). The weighting coefficients of the sensors 56 and 58 would be of opposite sign to that of the sensors 52 and 54.

Using the same information gathered from sensors 52, 54, 56, 58, and 59, optimized information about the source 50 can be synthesized. Once again, the weighting coefficient for the sensor 59 would be small, because it contributes little useful information to analyzing the source 50. However, in this case the weighting coefficients for the sources 56 and 58 would be large, since they are optimally placed for measuring source 50. The weighting coefficients for the sources 52 and 54 would be of opposite sign, because they gather some useful information but also reflect brain noise from source 48 (which in this case is considered noise with respect to the source 50 of interest) and other sources.

The information gathered by the array of sensors 52, 54, 56, 58, and 59 may be combined with yet other weighting coefficients to measure other sources not illustrated in FIG. 4. Although in the hypothesized examples of FIG. 4, the sensor 59 contributed little of use in measuring either source 48 or 50, for other sources in different locations the sensor 59 may become the most highly weighted sensor and some or all of the sensors 52, 54, 56, and 58 may have lower weights and different signs.

Only one set of actual physical measurements using the sensors 52, 54 56, 58, and 59 is made to yield information about the sources 48 and 50. The analytical approach permits those measurements to be combined in several ways, by using different weighting coefficients, to obtain the information about the individual sources. It is therefore possible, when the computer is used for the computations, to make one measurement using the sensors, store the measured values in the computer, and then perform a large number of computations using that measured and stored experimental data to deduce information about the magnetic signals produced by different sources at a single instant in time. Subsequent experimental results for the sensors are similarly stored and processed, permitting an understanding of the operation of each of the sources over time, both as to their individual operation and as to any interactions that may occur between sources.

The examples just presented illustrate the philosophical basis of lead field synthesis. However, they are purposely made to be not complex to illustrate the principles and possibilities of the approach. The vector nature of the sources 48 and 50, the type of source operating, and the magnetic permeability and electrical conductivity of the air, skull, and brain matter have not been discussed. Nor have the exact sensor locations and orientations, and the detailed geometry of the brain been incorporated into this qualitative description.

The more general implementation of lead field synthesis requires a mathematical study of the interaction of electromagnetic sources and sensors. The response of a magnetic sensor to a current source in the brain is directly proportional to the current I induced in the sensor coil, $$I = K \int G(\bar{r}) \cdot H(\bar{r}) dv$$

where $G(\bar{r})$ and $H(\bar{r})$ are the sensor lead field and the magnetic field generated by the source current at position $\bar{r}$. $G(\bar{r})$ is a characteristic of the sensor, and $H(\bar{r})$ is calculated from the source and media properties, as will be described subsequently.

If the sensor output an array of sensors is represented as a vector $\vec{S}$ and the weight to be accorded each sensor is represented by a vector $\vec{w}$ of equal dimension, the scalar output signal V is the dot product of the weight and sensor output vectors:

$$V = \vec{W} \cdot \vec{S}$$

Thus, the lead field of a virtual sensor defined by the summation of the weighted outputs of an array of sensors is $$G_v = \sum_i \omega_i G_i$$

Figure 6:
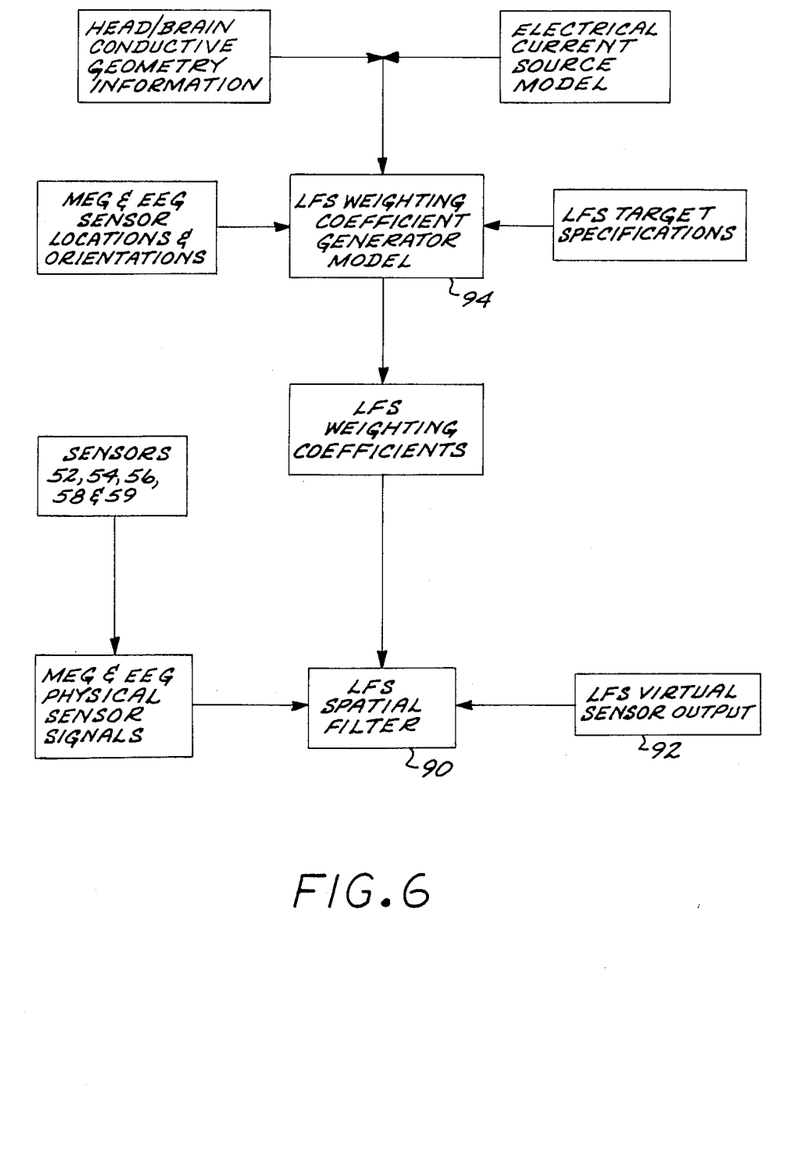
FIG. 6 is a block diagram for the process for performing lead field synthesis for brain signals.

A general approach to the determination of weighting coefficients is illustrated in FIG. 6. The physically measured sensor signals and the calculated weighting coefficients are supplied to the multiplying and adding functions, which are there termed a spatial filter 90. The present approach is a filter that selectively isolates and analyzes signals that are consistent with signals arising from particular volumes of the brain ("sources"). The result is the virtual sensor output 92, which can then be studied with respect to other virtual output signals, or with respect to physiological events or stimuli.

The calculation of the weighting factors w is made using a mathematical model of the interaction of electrical current sources in the brain and external sensors. The results of these analyses are manifested in the form of the weighting coefficients that are selected Thus, the basic computational approach discussed above and illustrated in FIGS. 5 and 6 does not change. Instead, the weighting coefficients are chosen by more sophisticated methods than the estimation approach discussed above.

The weighting coefficients are calculated from a mathematical model of the interaction between the magnetic activity and structure of the brain and external sensors, indicated at numeral 94. A model of the brain, with the attendant assumptions, is required because at this time there is no universally accepted concept and computational approach as to how the brain functions with respect to magnetic and electrical field generation, and how external sensors react to those fields.

However, the physical laws governing the electrical potentials and magnetic fields due to current flow in a volume conductor are known, and can serve to compute potentials and fields using a modeling approach to the head. Considerations required for most realistic models of the brain include those shown as input to the model 94, including, but not limited to, the sensor locations, orientations, and lead fields, the geometry and response to magnetic fields of the brain and skull, the conducting properties of the brain and skull, the nature of the current sources in the brain, and the geometry and orientation of the target source.

The relative physical locations of the sensors with respect to sites on the surface of the head and inside the brain matter may be determined in real time, simultaneous with the field measurements, in the manner illustrated in U.S. Pat. No. 4,793,355 or other acceptable manner. In general, a series of vectors defines points and locations with respect to each other, and the structure disclosed in the '355 patent permits such vector location information to be determined and stored by measurements in real time. The geometry of the outer surface of the head can also be measured and recorded in the manner disclosed in the '355 patent.

The nature of the interaction of an external sensor with a source within the head requires knowledge of the source field and the sensitivity pattern of the sensor, but also requires an understanding of the media and the effect of the media upon the electromagnetic field. The human head, which is a shaped brain mass within a skull of complex shape, has been modeled in various ways. In one of the simplest, the effect of the skull is largely ignored. In another, the skull is considered, but idealized as a sphere. The present lead field synthesis approach can be utilized with such models, which provide the weighting factors to be used.

The preferred model at the present time is a finite mesh model, wherein the outer shape of the skull is measured and digitized. The inner surface of the skull is obtained from this digitization by subtracting the approximate thickness of the skull itself from the measured points. The inner surface provides the boundary for an assumed homogeneous brain contained within the skull. In this model, the current source is described as an elementary current dipole. This model provides useful results, and can be run on computers that are readily available as this patent application is written. More sophisticated finite element models are known and are generally more accurate, but are presently less preferred because of the excessively long computing time required.

It is to be understood that the fundamental lead field synthesis approach is not dependent upon the use of any particular model. It is expected that, as new models are developed and greater computational power becomes available, even more sophisticated models will be utilized. In those cases, the weighting coefficients may change from those of the finite mesh model, but are still used as the linear combination factors for combining the outputs of the sensors of an array.

Continuing with the development of the finite mesh model, the solution for the magnetic field due to a primary current source within a bounded homogeneous conductor is found in the publication of F. Grynszpan and D. B. Geselowitz, "Model Studies of the Magnetocardiogram", *Biophysics Journal*, vol. 13, pages 911-925 (1978). Rephrasing their results for a current dipole source, the total magnetic field B(r), using the electrical potential at the surface of the object, $V(\bar{r}_s)$ and the conductivity $\sigma$:

$$G_i = B(r) = B_o(r) - \sigma \frac{\mu_o}{4\pi} \int_s V(r_s)n(r_s) \times \frac{r - r_s}{|r - r_s|^3} dS$$

$\bar{B}_o$, the magnetic field at measuring point $\bar{r}$ produced by a current dipole $\bar{Q}$ at $\bar{r}_o$ within an infinite homogeneously conducting space, is given by $$B_o(r) = \frac{\mu_o}{4\pi} Q \times \frac{r - r_o}{|r - r_s|^3} dS$$

The potential on surface S is $$V(r_s) = 2V_o(r_s) + \frac{1}{2\pi} \int_s V(r_s')d\Omega(r_s')$$

where $d\Omega$ ($\bar{r}_s'$) is the solid angle subtended at $\bar{r}_s$ by surface element dS ($\bar{r}_s$), and $V_o$ is the potential within an infinite homogeneously conducting space due to a current dipole $\bar{Q}$:

$$V_o(r) = \frac{1}{4\pi\sigma} Q \cdot \frac{r - r_o}{|r - r_o|^3}$$

As shown by M. S. Hämäläinen and J. Sarvas in their publication "Feasibility of the Homogeneous Head Model in the Interpretation of Neuromagnetic Fields", *Phys. Med. Biol.*, vol. 32, pages 91-97 (1987), if the boundary is represented by a finite mesh consisting of n triangular elements, the first-presented equation becomes:

$$B(r) = B_o(r) - \frac{\mu_o \sigma}{4\pi} \sum_{i=1}^{n} V(c_i)n(c_i) \times \frac{r - c_i}{|r - c_i|^3} \Delta S_i$$

where $\bar{c}_i$ is the center point of a triangular element, n is the outward-pointing normal vector, and $\Delta S_i$ is the surface of the ith triangular surface element.

Similarly, the equation for $V(\bar{r}_s)$ may be expressed in discrete form by letting $\omega ij$ be the solid angle subtended by the jth triangular element at center point $\bar{c}_i$. The potential at each facet is $$V(c_i) \simeq 2V_o(c_i) + \frac{1}{2\pi} \sum_{\substack{j=1 \\ j \neq i}}^{n} \omega_{ij}V(c_j)$$

$i = 1, 2 \ldots n$

This equation is solved after transformation of the surface element potentials with a set of linear equations $$\alpha_i = \sum_{j=1}^{n} A_{ij}V_j \: i = 1, 2 \ldots n$$

where $$\alpha_i = 2V_o(c_i), \: V_j = V(c_j),$$

$$A_{ij} = \begin{cases} -\frac{1}{2\pi} \omega_{ij} & \text{if } i \neq j \\ 1 & \text{if } i = j \end{cases}$$

A unique solution is provided by replacing $A_{ij}$ with $A'_{ij}+1/n$. The system of equations is solved by matrix inversion, and the surface potentials are substituted back into the discrete $B_r$ equation.

Different models may be developed to calculate the weighting coefficients for several reasons. First, different models may be applicable to different parts of the brain. Second, the models themselves may require refinement as to assumptions used and mathematical techniques used to solve them. As with many theories, as the model becomes more complex and realistic, its use may be limited by the mathematical techniques available for its solution.

Figure 7:
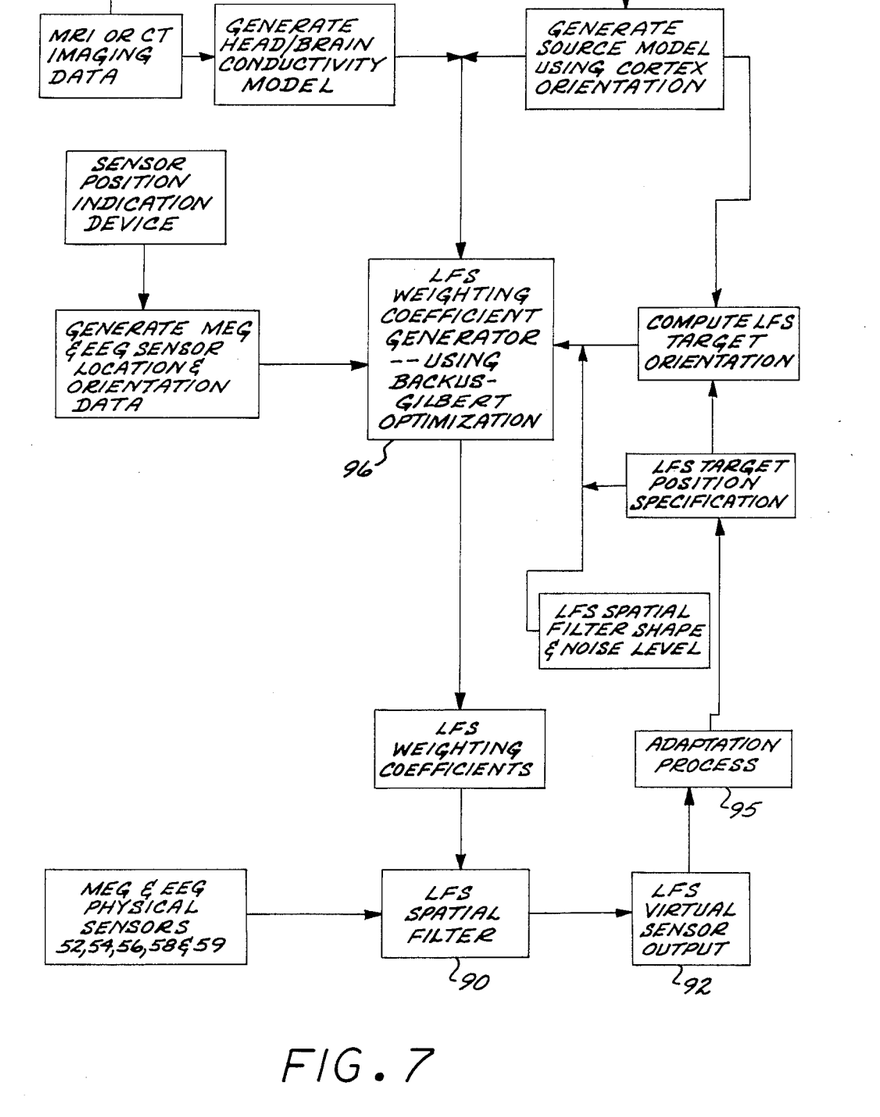
FIG. 7 is a block diagram for an augmented process for performing lead field synthesis for brain signals.

Some further development of the lead field synthesis methodology is presented in FIG. 7, where the elements already discussed with respect to FIG. 6 carry similar numerals. To provide positioning information in an automated manner, the position indication device of the '355 patent is used. Direct imaging data from other sources is used in the geometrical analysis of the head.

Additionally, an adaptive analysis capability is provided, numeral 95. That is, the computer can alter the model used the assumptions of the model, or the values used in the calculation, to determine whether these changes result in a more consistent result.

The augmented model further provides for a Backus-Gilbert optimization, numeral 96. A fundamental problem in ascertaining the signal associated with a particular location is that the number of potential signal and noise sources in the brain is far greater than the number of sensors that may be arrayed external to the brain to measure those signals. There is therefore always some uncertainty of the signal associated with a target location in light of brain and instrument noise.

The theory of Backus and Gilbert relates the selectivity of a solution to the noise experienced by the sensors. A review of this theory is found in the publication by R. L. Parker, "Understanding Inverse Theory", *Ann. Rev. Earth Planet. Sci.*, vol. 5, pages 35–64 (1977). The methodology effectively rotates the spatial filter vector obtained from the forward solution described above, away from the interfering sources such that the projection of the noise sources onto the filter vector is minimized, while maintaining as large a projection for the target source as is possible.

Developing the Backus-Gilbert theory in a three-dimensional model, the optimum weight vector $\vec{W}$ is found by solving the matrix minimization $$\min_{w} \vec{W}^T A \vec{W}$$

subject to $$\vec{W}^T B \vec{W} = 1$$

where $$A_{ij} = \int_\Omega G_i(r_o) G_j(r_o) (r_o - r_t)^2 d\Omega$$

and $$B_{ij} = \int_\Omega G_i(r_o) G_j(r_o) d\Omega$$

$r_o$ is any point within the head or body, and $r_t$ is the target location, the region of particular interest. Using a Lagrange multiplier and differentiating with respect to each of the variables leads to a simple matrix equation for the unknown vector of weights W. These weights are used as the multipliers, as for example the multipliers $w_{52}$, $w_{54}$, $w_{56}$, $w_{58}$, and $w_{59}$ of FIG. 5.

Figure 8:
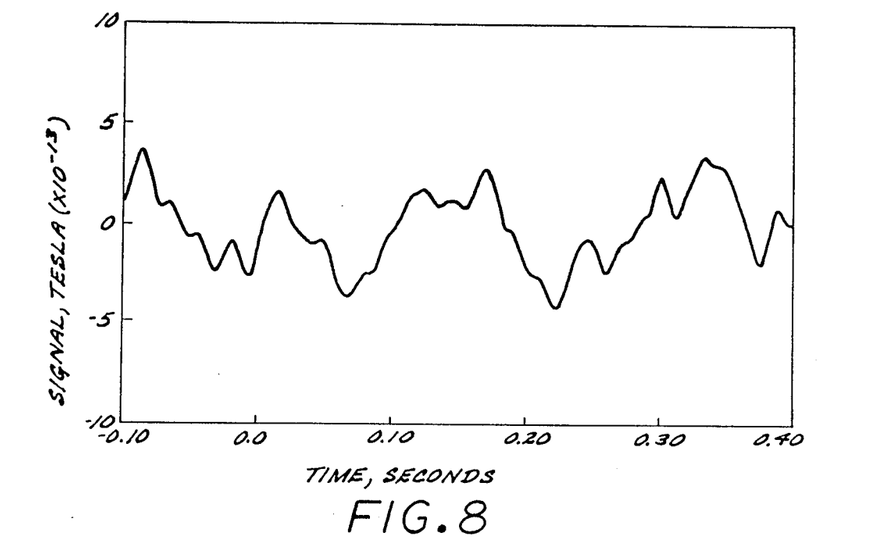
FIG. 8 is a graph of the measured signal as a function of time for a sensor positioned proximate to the head of a person.

The approach described in the preferred embodiment was applied to the analysis of recordings of brain signals made with a 14-sensor biomagnetometer. An experiment was conducted in which a person's brain response to an external auditory stimulus was measured by the 14 magnetic sensors and recorded. FIG. 8 is an exemplary output signal from one of the 14 physical sensors, which in this case was positioned over one of the extrema and therefore thought to be optimally positioned. (The other 13 physical sensors also produced output signals as a function of time which were recorded, but these signals are not reproduced here.) Using the brain coordinates determined for the response to an auditory stimulus, a spatial filter was computed using the approach of the preferred embodiment, and applied to the 14 output signals.

Figure 9:
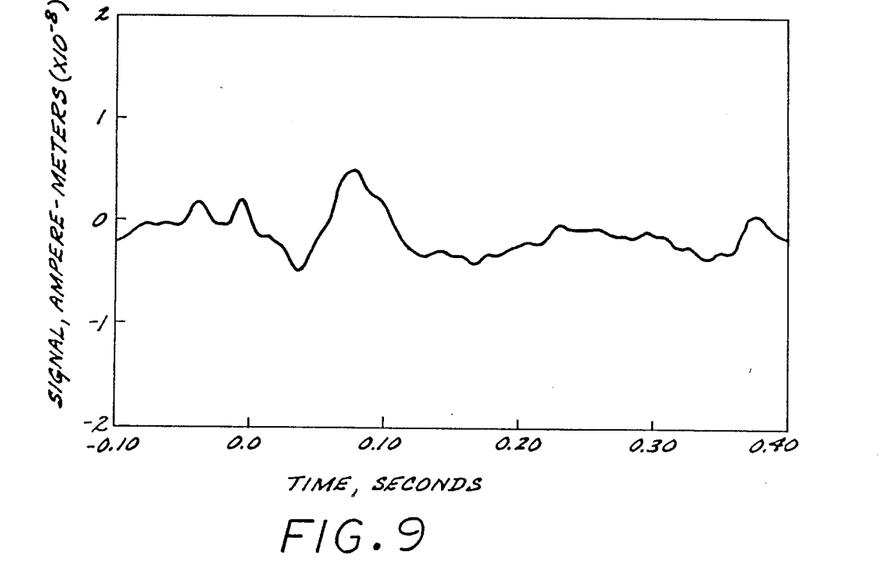
FIG. 9 is a graph of a synthesized virtual sensor signal as a function of time.

FIG. 9 is the computed virtual signal, calculated as the weighted sum of the 14 individual sensor output signals. The response to the auditory stimulus, which was applied at 0.0 seconds, is not distinguishable from the brain noise in the physical sensor trace, FIG. 8, nor was it distinguishable in any of the other physical sensor traces. However, the brain response can be clearly discerned in the virtual sensor trace, FIG. 9. This result demonstrates that brain noise has been sufficiently suppressed by the present approach that source signals of interest can be discerned. With this capability to measure the response of the brain to the external stimulus, it is then possible to conduct experiments that determine the change in response of the brain to changes in the auditory signal, repetition of the auditory signal, or other factors under study.

The lead field synthesis approach provides a valuable new approach for analyzing the magnetic signals (or electrical signals, with the appropriate sensors) generated within the human body, and particularly within the brain or the heart. The approach of the invention is used to analyze data collected from the sensors, to calculate the behavior of a source of interest while minimizing the effects of other sources within the brain. Although a particular embodiment of the invention has been described in detail for purposes of illustration, various modifications may be made without departing from the spirit and scope of the invention. Accordingly, the invention is not to be limited except as by the appended claims.

What is claimed is:

1. A process for sensing and evaluating signals emanating from the brain of a subject, comprising the steps of:

providing an array of magnetic field sensors disposed external to a head of said subject at known locations;

measuring a signal strength detected by each of said sensors;

multiplying the signal strength measured by each of said sensors times a weighting coefficient for that sensor selected to focus the sensitivity of the array of said field sensors on a selected location in the brain, to determine a virtual sensor contribution for each of said sensors; and adding together the virtual sensor contribution of each of said sensors, to define a virtual sensor signal.

2. The process of claim 1, wherein each of said sensors includes a superconducting quantum interference device.

3. The process of claim 1, including, after the step of adding, the additional step of:

correlating the virtual sensor signal with a physiological activity.

4. A process for sensing and evaluating signals emanating from a body of a subject, comprising the steps of:

measuring a signal strength detected by each sensor of an array of electromagnetic sensors placed proximately to said body of a subject; and calculating a virtual sensor signal for the array, as a sum, over all of said sensors, of a product of a weighting coefficient for each said sensor times the signal measured for that sensor, the weighting coefficients being selected to focus the array of sensors on a selected location in the body.

5. The process of claim 4, wherein the weighting coefficient for each of said sensors is selected to optimize a contribution to a virtual signal of a selected target source relative to signals not produced by that target source.

6. The process of claim 4, wherein the sensors are placed proximately to a head of the subject.

7. The process of claim 4, wherein the sensors are placed proximately to a chest of the subject.

8. A process for sensing and evaluating electromagnetic signals emanating from a body of a subject, comprising the steps of:

providing an array of electromagnetic field sensors disposed external to a body of a subject at known locations;

determining a weighting coefficient applicable to each of said sensors, the step of determining including the steps of characterizing a geometry of the body, characterizing a nature of the magnetic fields emanating from possible sources in the body, characterizing a medium through which the magnetic fields propagate, formulating a mathematical model of the response of said sensors to a source within the body, and calculating each of said weighting coefficients from the model;

measuring the signal strength detected by each of said sensors;

multiplying the signal strength measured by each of said sensors times the calculated weighting coefficient for that sensor to determine a virtual sensor contribution for each of said sensors; and adding together said virtual sensor contributions of each of said sensors, to define a virtual sensor signal.

9. The process of claim 8, wherein the calculated weighting coefficient for each of said sensors is selected using the mathematical model to optimize a contribution to the virtual signal of a selected target source, relative to signals not produced by the target source.

10. The process of claim 8, including, after the step of adding, the additional step of:

correlating the virtual sensor signal with physiological information.

11. The process of claim 8, wherein each of said sensors includes a superconducting quantum interference device.

12. The process of claim 8, wherein the mathematical model is a finite mesh model.

13. The process of claim 8 wherein each of said sensors is placed proximately to a head of the subject.

14. The process of claim 8, wherein each of said sensors is placed proximately to a chest of the subject.

* * * * *